(12) United States Patent
Mansour

(10) Patent No.: US 8,142,444 B2
(45) Date of Patent: Mar. 27, 2012

(54) CIRCUMCISION CLAMP AND SURGICAL KIT

(76) Inventor: Karim Mansour, Del Mar, CA (US)

( * ) Notice: Subject to any disclaimer, the term of this patent is extended or adjusted under 35 U.S.C. 154(b) by 0 days.

(21) Appl. No.: 12/552,872

(22) Filed: Sep. 2, 2009

(65) Prior Publication Data

US 2010/0114112 A1    May 6, 2010

Related U.S. Application Data

(63) Continuation-in-part of application No. 11/704,804, filed on Feb. 9, 2007, now abandoned.

(51) Int. Cl.
*A61B 17/32* (2006.01)
(52) U.S. Cl. ...................................... 606/118
(58) Field of Classification Search .......... 606/118, 606/157, 167, 131, 201, 120, 205–208, 45, 606/119; D24/143; 269/237; 24/522, 528; 227/180.1
See application file for complete search history.

(56) References Cited

U.S. PATENT DOCUMENTS

| | | | | |
|---|---|---|---|---|
| 408,586 A | * | 8/1889 | Coleman | 72/317 |
| 2,646,047 A | * | 7/1953 | Bronstein | 606/118 |
| 3,789,848 A | * | 2/1974 | Honjyo | 606/118 |
| 5,897,490 A | * | 4/1999 | Fox et al. | 600/227 |

* cited by examiner

*Primary Examiner* — Ryan Severson
*Assistant Examiner* — Tin Nguyen
(74) *Attorney, Agent, or Firm* — Biotech Beach Law Group PC

(57) ABSTRACT

A circumcision clamp and surgical kit including a rod having a bell-shaped member at a first end for receiving the head of a penis and an engagement structure at an opposing end; a base including: two hinged arms, wherein when closed the arms include at least three upwardly tapered apertures aligned along an arc and having unequal diameters, wherein each upward taper is complementary to the bell-shaped member, at least three fulcrum recesses aligned along an arc and in radial alignment with the at least three apertures; a lever including: a proximal end in radial alignment with the at least three apertures and the at least three fulcrum recesses, a distal end including a fulcrum foot complementary to the at least three fulcrum recesses and adapted for engagement with the engagement structure of the rod; and an adjustment structure for raising and lowering an engaged rod by pivoting the lever at one of the at least three fulcrum recesses.

9 Claims, 12 Drawing Sheets

CIRCUMCISION CLAMP AND SURGICAL KIT

CROSS-REFERENCE TO RELATED APPLICATIONS

This application is a continuation-in-part of Ser. No. 11/704,804 filed Feb. 9, 2007, which is incorporated herein by reference in its entirety.

FIELD OF THE INVENTION

The present invention relates generally to surgical clamping devices, and more specifically to a circumcision clamp for performing a circumcision operation or procedure and related surgical kits.

BACKGROUND OF THE INVENTION

The foreskin or prepuce is a retractable double-layered fold of skin and mucous membrane that covers the glans penis and protects the urinary meatus when the penis is not erect. Often, the foreskin of the penis is removed through a procedure called circumcision.

Because of the widespread use and practice of circumcision, a variety of instruments and techniques have been employed to perform the operation. These instruments and techniques achieve the goal of removing excess foreskin from the penis with reduced trauma, pain, blood loss, and discomfort. Typically the devices securely hold the prepuce prior to, during, and after surgical removal thereof. Certain of these are members of a group of circumcision devices referred to as the "bloodless" type. They clamp and squeeze the prepuce to prevent blood flow to the tissue that is to be removed. Because blood flow to the prepuce is stopped, little or no bleeding occurs at the wound site formed by the procedure. However, these devices can be difficult to use. Many of these clamps require threading both layers of the foreskin through a fixed aperture or port. This technique is difficult to perform, especially for newly admitted physicians. Often only one of the layers is properly threaded through the port, resulting in an uneven circumcision.

One such "bloodless" circumcision clamp is disclosed in U.S. Pat. No. 3,392,728. This device includes a base having a single port at the proximal end and a stud bolt positioned at the distal end, a rod-like member having a cross pin at an upper end, a bell shaped member at the lower end, and an arm member pivotally mounted to the base and adapted for engagement with the cross pin at the proximal end and slidably mounted to the stud bolt at the distal end. The majority of the rod-like member is able to pass through the single port, but the lip of the bell is formed large enough to prevent passage through the single port. As a consequence, when the smaller end of the bell member is inserted into the port and the member is drawn through as far as possible, the lip of the bell presses tightly around the circumference of the port. The arm member is pivotally positioned on the base such that lowering the distal end raises the proximal end. The arm member is raised and lowered by tightening or loosening a nut along the stud bolt. Operation of the device includes determining which device to utilize by evaluating the size of the single port offered by each base, drawing the prepuce over the lip of the of the bell-shaped member, feeding the rod through the single port while keeping the prepuce along the outer portion of the bell, engaging the cross pin, and tightening the nut until the prepuce is sufficiently pinched against the rimmed single port.

Current devices are deficient in several respects; first, the base member includes only a single port, which does not accommodate a wide variety of patients. Therefore the practitioner is required to either purchase multiple devices for the range of potential patients or utilize a device beyond its intended patient range. Second, it is often difficult for the practitioner to perform, and painful for the subject to undergo, the fitting of the prepuce through the single fixed port in the base member. Third, frequently only one of the two folds of the prepuce is correctly inserted through the port resulting in an uneven circumcision. Fourth, it can be awkward for a practitioner to effectively raise the bell member when clamping the prepuce, resulting in uneven clamping due to misalignment. Therefore, there remains a need to develop improved devices for performing circumcisions.

SUMMARY OF THE INVENTION

The present invention addresses the deficiencies inherent to current devices by providing an easier-to-use, more versatile clamp that will reduce the likelihood of uneven circumcisions. More specifically, the present invention provides a base that can be closed around the foreskin for effective and precise clamping of the foreskin between the bell-shaped member and a tapered aperture. These advances permit both folds of the prepuce to be easily clamped. Further the circumcision clamps reduce torsional stress compared to traditional devices and thus reduce the likelihood of pain or discomfort while performing the procedure. Additional beneficial features are related to each of the circumcision clamps provide herein.

The present invention provides at least two aspects. A first aspect includes a base having multiple tapered apertures aligned along an arc and in radial alignment with multiple fulcrum recesses. The tapered apertures are provided in different diameters to accommodate various penis sizes. A lever pivots along the fulcrum recess using a fulcrum foot. Pivoting the lever such that the proximal end approaches the base raises the distal end, which is engaged to a rod having a bell-shaped member extending through one of the tapered apertures, which receives the head of the penis and permits the prepuce to extend over the outer wall of the bell. The base, which is hinged to provide two halves, reversibly opens and closes to clamp the tapered apertures around the bell-shaped member. Further, by raising the rod, the bell-shaped member tightens against the rim of the tapered aperture thereby securing the prepuce of the penis between the bell-shaped member and the base. As such the prepuce may be excised above the base.

In another aspect of the present invention, a circumcision clamp is provided including a rod having a bell-shaped member at one end and a engagement structure at the opposing end, a base having two arms hinged at one end and forming at least two rimmed apertures when in the closed position, and an actuating structure including two elongated members including a handle at one end and at the opposing end one member adapted for engagement with the engagement structure for raising the rod and the other member adapted for placement in a recess or throughbore of the base for stabilizing the device. The bell-shaped member receives the prepuce and the base is capable of closing around the received prepuce for ease of use. The engagement structure engages the actuating structure such that the rod may be lifted when the handle of the actuating structure is squeezed. The actuating structure may be locked in the closed or squeezed position.

In some embodiments the base of the device is bifurcated, with the two resulting arms hinged at one end and capable of reversible engagement to one another at the opposite end. When engaged the two arms are substantially parallel. The reversible-engagement capability of the arms provides a distinct advantage over current technology, as it allows the operator to manipulate the base around the patient, instead of, as is the current practice, drawing the patient through a single port of the base. The diameters of the rimmed apertures formed by the engaged base arms are different from one another, though the diameters of the rimmed apertures are in all cases smaller than the largest portion of the bell-shaped member or outer lip. This multiplicity of rimmed apertures enables the device to accommodate patients of various sizes, eliminating the need to provide several different bases, a requirement of previous devices. Positioned in close proximity of each rimmed aperture is a recess or throughbore capable of receiving the distal end of one of the elongated members that form the actuating structure.

In some embodiment the actuating structure includes two members hinged near their midpoints or mid region. Each elongated member has a distal and proximal end, with the proximal ends forming a handle. The two members are constructed such that when the proximal ends are maximally proximate and substantially parallel, the distal ends are maximally opposed. One of the distal ends is formed for placement in the recess or throughbore of the base, and the other distal end is formed to engage the rod's engagement structure. The actuating structure is actuated by squeezing the handle. In some embodiments the actuating structure includes a locking means to lock the actuating structure in the closed or squeezed position.

In another aspect of the present invention a circumcision kit is provided including a circumcision clamp and a medical instrument such as a scalpel. The kit can also include additional surgical instruments such as, for example, a hemostat and the like. The kit can be provided as a one-time use device or a reusable kit.

In another aspect of the present invention a method of performing a circumcision is provided including providing a circumcision clamp of the present invention, placing the head of a patient's penis in the bell-shaped member, pulling the foreskin over the outer portion of the bell-shaped member, closing the base around the bell-shaped member covered with the foreskin, engaging then raising the rod such that the bell-shaped member is tightened against the aperture rim, inserting one of the distal ends of the actuating structure in the recess of the base and engaging the rod's engagement structure with the opposing distal end, squeezing the handle to cause the actuating structure to raise the bell-shaped member and foreskin against the rimmed aperture, and cutting the foreskin above the base.

BRIEF DESCRIPTION OF THE DRAWINGS

Those of skill in the art will understand that the drawings, described below. are for illustrative purposes only. The drawings are not intended to limit the scope of the present teachings in any way.

FIG. 9A is a lowered configuration showing the bell-shaped member 14 substantially below the base 120. In FIG. 9B, the surgical clamp 100 is shown in a raised configuration. The proximal ends 122 a,b of the actuating structure 118 are maximally proximate when the distal ends 124 a,b are maximally opposed. In the raised configuration the bell-shaped member 14 is no longer substantially beneath the base 120.

FIG. 10A is a front plan view of the rod 12 depicted in FIGS. 1 and 9 showing the bell-shaped portion 14 at one end and the engagement structure 16 at the opposing end, FIG. 10B is a side elevational view of the rod depicted in FIGS. 1 and 9, FIG. 10C is back plan view of the rod 12 depicted in FIGS. 1 and 9 turned on its side and FIG. 10D is a bottom plan view of the rod 12 depicted in FIGS. 1 and 9 showing the inner region 15 of the bell-shaped member 14, which is fabricated to receive the head of a penis.

FIG. 12A is a top plan view of the distal end 124a of the upper member 126a, FIG. 12B is a top plan view of the distal end 124b of the lower member 134b. FIG. 12C is a side elevational view of the actuating structure 118 depicted in FIG. 9. The actuating structure is shown in an open position in FIG. 12C and a closed or squeezed position in FIG. 12D. The actuating structure 118 includes two elongated members 134a and 134b hinged 136 at about their midpoint The proximal end 122 includes a handle 136 and a locking means 138 for locking the upper 134a and lower 134b members in a closed configuration. The distal end 124a of the upper elongated member 134a is adapted for engagement with an engagement structure 116 by providing a hook-like configuration for hooking a cross pin. The distal end 124b of the lower elongated member 134b is adapted for placement in the recess 28.

DETAILED DESCRIPTION OF THE PREFERRED EMBODIMENTS

Figure 1:
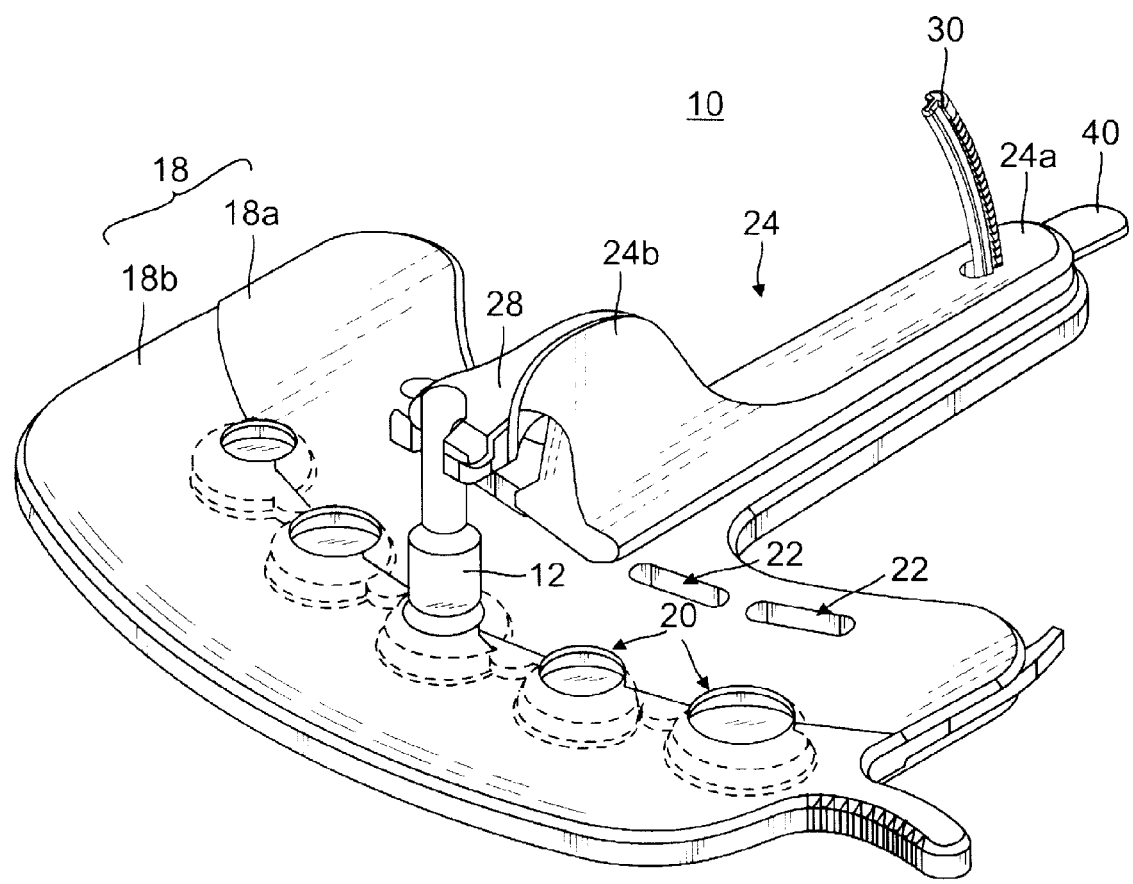
FIG. 1 is a perspective view of a circumcision clamp 10 depicting the two hinged arms (18a, 18b), which form the base 18, a lever 24 having a proximal end 24a through which is inserted the adjustment structure 30 for adjusting or locking the lever 24 in pivotal orientation to the base 18. The distal end 24b of the lever 24 engages the rod 12 to pivotally raise or lower the rod 12. Apertures 20 and fulcrum recesses 22 are each shown aligned along an arc such that each aperture 20 includes a corresponding fulcrum recess 22, which acts as a pivot point for raising or lowering the distal end 24b and thus the rod 12.

In contrast to previous circumcision clamps, embodiments of the present invention include devices that more easily and accurately clamp the foreskin prior to performing a circumcision. As will be envisioned by one skilled the art to which the present invention belongs, the physician or user is able to clamp the foreskin more effectively by closing the arms of the base around the foreskin instead of relying on the user's ability to thread the foreskin through a fixed aperture. Further, by providing a plurality of apertures of varying sizes, the single circumcision clamp can be used with a variety of penis sizes. The various aspects and embodiments have further advantages according to their particular features which shall be discussed in more detail below.

FIGS. 1-8 and 10 provide a first aspect of a circumcision clamp 10, which includes a base 18 including a plurality of apertures 20 aligned along an arc, which are each assigned a fulcrum recess 22. The aperture 20 is selected by rotating a lever 24 in a circular fashion around its proximal end 24a until a fulcrum foot 26 mates with the fulcrum recess 22. The lever 24 is then pivoted at the fulcrum recess 22 to raise and lower its distal end 24b and thus the rod 12. Further, by providing a base 18 that opens and closes, apertures 20 may be opened then closed around the rod 12.

FIGS. 9-12 provide a second aspect of a circumcision clamp 100 including a base 120 including a plurality of apertures 126 and an actuating structure 118 that raises a rod 12 with bell-shaped member 14 by squeezing together a handle portion that is formed from the proximal ends 122a, b of two elongated members making up the actuating structure 118. The distal portion 124b of one elongated member substantially surrounds the rod 12 by placement in recess 128 that surrounds at least in part, the aperture 126 and the distal portion 124a of the second elongated member grasps the engagement structure 16 of the rod 12.

Embodiments of the present invention can be made from a variety of materials and techniques used in the medical device arts. Exemplary materials include metals, metal alloys, ceramics, plastics, and the like. In some embodiments, the clamp 10, 100 is provided in a sterilized form and in some embodiments the clamp 10, 100 may be autoclaved for repeated sterilization.

In embodiments utilizing metals or semi-metals, the materials may be chosen according to the desired characteristics. Examples can include aluminum, titanium, iron, nickel, copper, zinc, silver, tungsten, platinum, gold, combinations thereof, alloys thereof, and the like. In embodiments that include metal alloy materials, the alloy can be, for example, Al—Li, alnico, duralumin, magnalium, nambe, silumin, steel, AA-8000, or the like.

In embodiments that include ceramic materials, the material can be, for example, alumina, boron carbide, silicon carbide, tungsten carbide, or the like.

In embodiments that include plastic materials, the plastic materials can include, for example, thermoplastics, such as, for example, acrylonitrile butadiene styrene plastics (ABS), acetals, acrylic (Perspex), acrylo-nitrile (nylon), cellulosics, fluoroplastics, high-density polyethylene (HDPE), low-density polyethylene (LDPE), Noryl, polyarylates, polyarylsulfones, polybutylenes, polybutylene terepthalate (PBT), polycarbonates, polyesters, polyetherimides, polyetherketones, polyethylene (polythene), polypropylene, polyallomers, polyethylene terephalate, polyimides, polyamide-imides, poly vinyl acetate (PVA), poly vinyl chloride (PVC), polystyrene, polysulfones, Styrene, ABS PTFE (Teflon), and the like.

In embodiments that include plastic materials, the plastic materials can be, for example, thermosets, such as, for example, alkyd polyesters, allyls, bakelite, epoxy, melamine, phenolics, polybutadienes, polyester, polyurethane, silicones, ureas, and the like. Likewise, the plastic materials can include bioplastics. Bioplastics are a form of plastics derived from renewable biomass sources, such as vegetable oil, corn starch, pea starch, or microbiota, rather than traditional plastics that are often derived from petroleum. Types of bioplastics suitable for use with embodiments of the invention include, for example, polylactide acid (PLA) plastics, poly-3-hydroxybutyrate (PHB), polyamide 11 (PA 11), bio-derived polyethylene, and the like. Such materials are known in the plastic arts and can be molded according to known methods such as injection molding and the like.

In some embodiments, the device 10, 100 or parts thereof are coated with a material to change its, for example, surface properties, or the like. For example, the device 10, 100 can be coated with an antibacterial material. In certain embodiments the device 10, 100, such as the base 18, 120, is made from transparent materials or semi-transparent materials, such as transparent or semi-transparent plastics.

Although the terms used herein are known by those skilled in the art to which the present invention belongs, the following definitions may prove useful to the less skilled artisan.

The term "upwardly tapered" as used herein refers generally to a cone shape that narrows when proceeding upward. An upwardly tapered aperture has a larger diameter or opening at the bottom compared to the top. An upwardly tapered aperture includes a side wall or rim that is angled greater than 90 degrees and less than 180 degrees from bottom to top.

The term "aligned along an arc" or "in arced alignment" as used herein refers to a series of features that are aligned such that they can form a portion of a circumference of a circle. Apertures that are "aligned along an arc" permit a single lever to selectively access each aperture by rotation around a central point or region, which is typically at the proximal end of the lever. When providing fulcrum recess aligned along an arc a single pivot point or region is provided for each of a series of apertures. Thus the apertures and fulcrum recesses may each be aligned along an arc such that a lever may rotationally select an aperture by rotating to a corresponding fulcrum recess.

The term "rotational selection", "rotationally selected" or "selected by rotation" refers to the selection of an aperture by rotating the lever either clockwise or counter-clockwise around a central point or region, such as the proximal end of the lever. An example of rotational selection may be performed by removing the fulcrum foot from a first fulcrum recess, rotating the lever clockwise or counter-clockwise and inserting the fulcrum foot in a second recess.

The term "radial alignment" or "alignment along a radius" as used herein refers to the positioning along a radius extending from an arc. A recess is in radial alignment with an aperture if the aperture is provided along an arc and its radius intersects the recess. A lever is in radial alignment with a series of apertures if the lever can be rotated, either clockwise or counter-clockwise between apertures.

Circumcision Clamp with Rotational Selection of Aperture

Referring collectively to FIGS. 1-8, and 10 a preferred circumcision clamp 10 includes a rod 12 including a bell-shaped member 14 at a first end for receiving the head of a penis and an engagement structure 16 at an opposing end. The circumcision clamp 10 also includes a base 18 including two hinged arms 18a, 18b which when closed form at least three upwardly tapered apertures 20 aligned along an arc and having unequal diameters. The upward taper is preferably complementary to the bell-shaped member 14 such that the bell-shaped member 14 may squeeze or tighten against the base 18 when the rod 12 is raised upward through the aperture 20. At least three fulcrum recesses 22 are aligned along an arc having a shorter arc length than that of the at least three tapered apertures 20. A lever 24 including a proximal end 24a and distal end 24b is positioned over the base 18 and includes fulcrum foot 26 complementary and for placement in the fulcrum recess 22, which allows the lever 24 to pivot at the fulcrum foot 26. Thus, lowering the proximal end 24a raises the distal end 24b, which raises the rod 12 through the aperture 20 until the bell-shaped member 14 prevents further upward movement such as by placement against the rim of the tapered aperture 20. An adjusting structure 30 may adjust or lock the position of the proximal end 24a and thus the height of the distal end 24b and rod 12.

Referring to FIG. 1, five tapered apertures 20 are shown with a rod 12 extending upward through a third aperture 20. It is apparent that the lever 24 is in a raised configuration since the proximal end 24a of the lever is substantially parallel to the base 18, which raises the distal end 24b of the lever 24 and thus the rod 12 through the aperture 20. As such, raising the proximal end 24a lowers the distal end 24b and thus lowers the rod 12 through the aperture 20, which releases the patient from the circumcision clamp 10.

Figure 2:
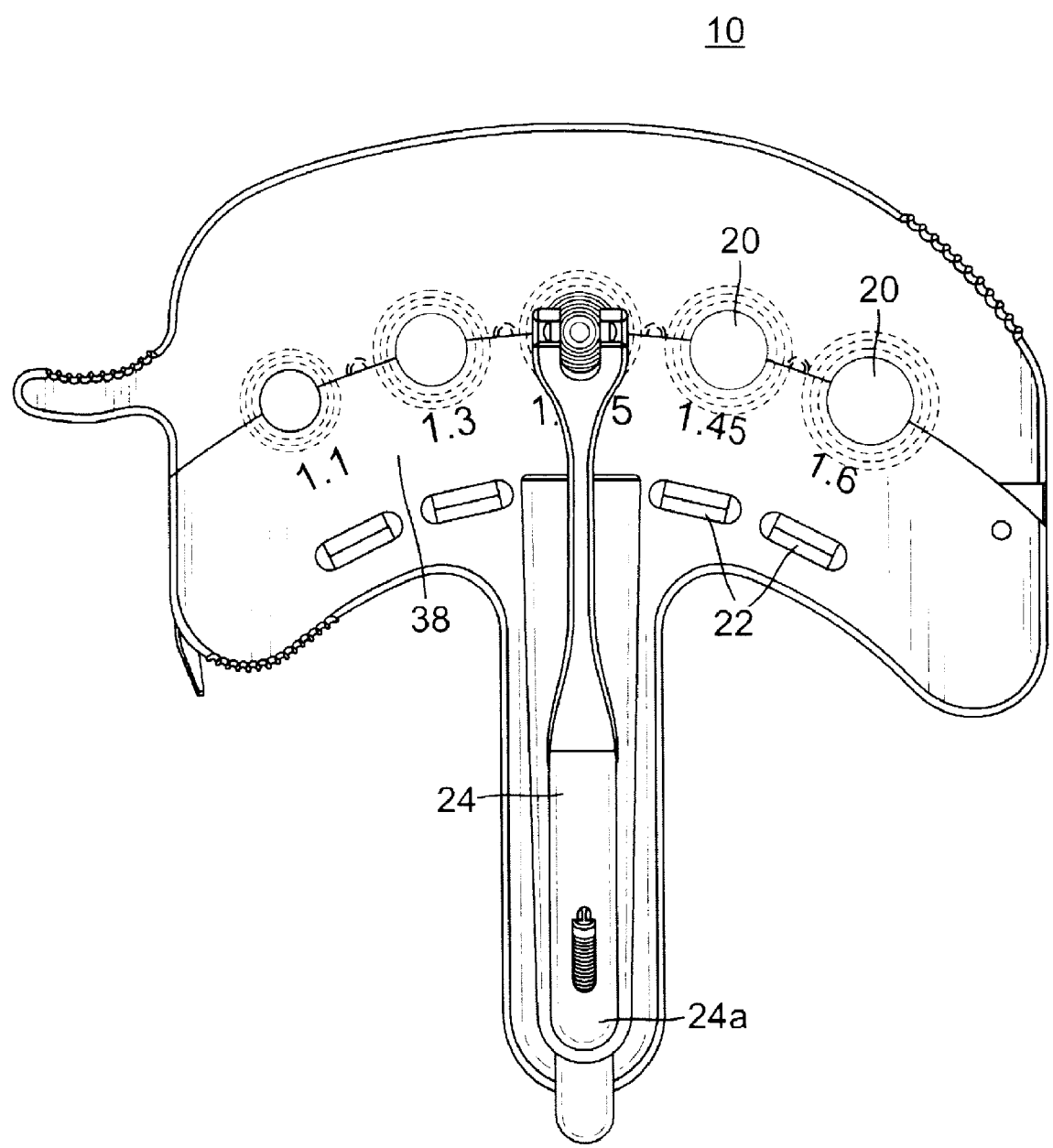
FIG. 2 is a top plan view of the circumcision clamp 10 further demonstrating the apertures 20 and recesses 22, each aligned along an arc to permit the radial selection of an aperture 20 by the lever 24. Visual indicial 38 correspond to the size of the apertures 20, which vary in diameter.

Preferably, assigned to each aperture 20 is a recess 22 for selection by the lever 24. However, in other embodiments the recess 22 is a track that extends along an arc for use with more than one aperture 20. FIG. 2 depicts a preferred embodiment demonstrating the arced alignment of the tapered recesses 20 and the arced alignment of the fulcrum recesses 22, which permits rotational selection by the lever 24 around the proximal end 24a. As such, apertures 20 may be individually chosen by rotating the lever 24 around the proximal end 24a to the corresponding fulcrum recess 22. Thus the apertures 20 may be rotationally selected by rotating of the lever 24 clockwise or counter-clockwise around a circumference. Fulcrum recesses 22 may be formed by traditional milling or injection moulding techniques when forming the base half 18a. Indicia 38 may be provided to supply the user with information, such as the size or relative size of a corresponding aperture 20 and the like.

Figure 3:
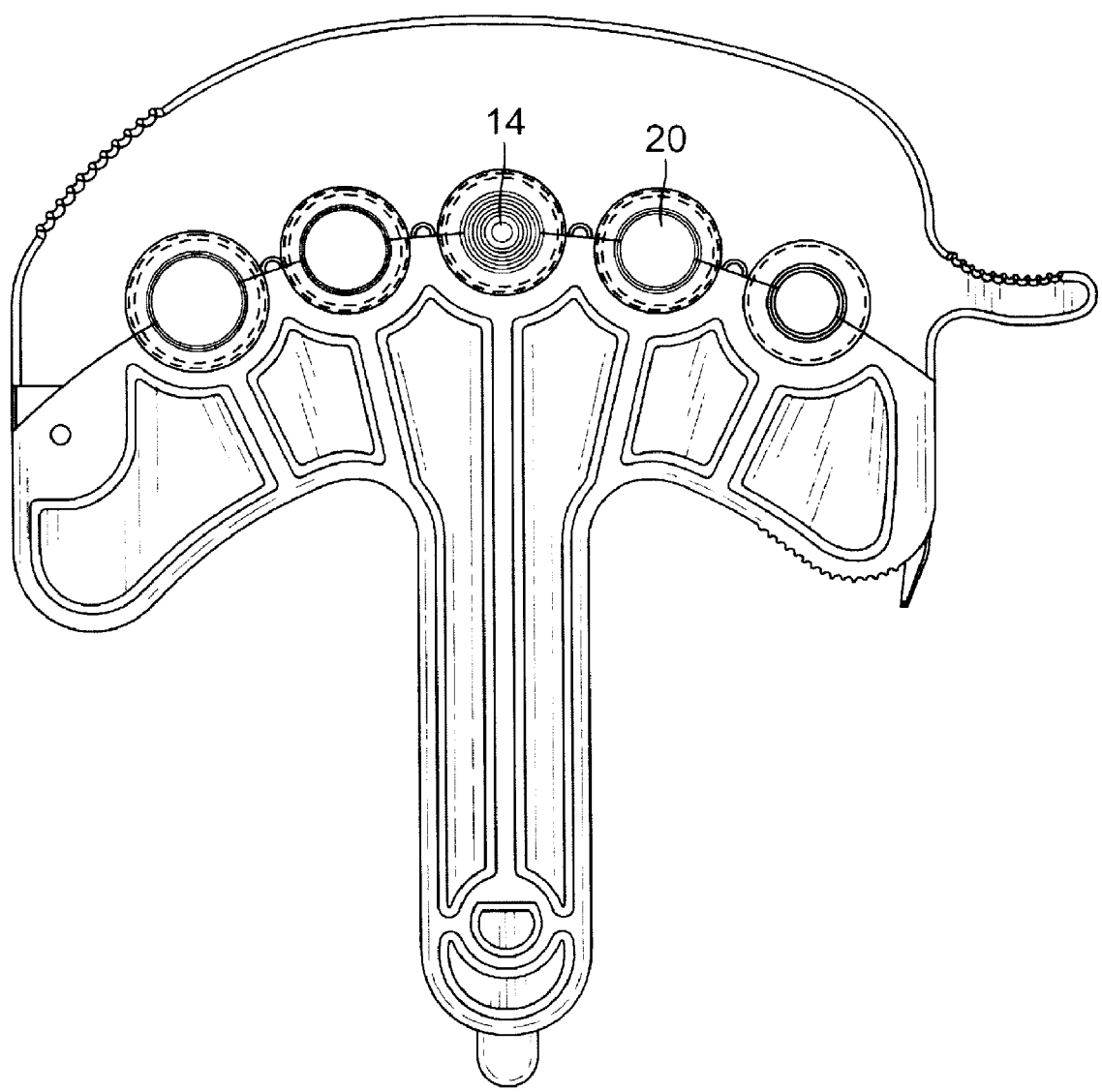
FIG. 3 is a bottom plan view of the circumcision claim 10 showing the upwardly tapered apertures 20 and bell shaped member 14.

FIG. 3 provides a bottom view of the circumcision clamp which demonstrates the upwardly tapered apertures 20. As shown in FIG. 3 the preferred tapered apertures are generally cone-shaped and complementary to the bell shaped member 14. Though depicted as circular or cone shaped, the apertures 20 may be provided in any desired shape such as triangular or pyramid-shaped or as a polygon having four, five or more sides. The aperture 20 is preferably shaped complementary to the lower portion 14 of the rod 12, which in the preferred embodiment is bell-shaped.

Figure 4:
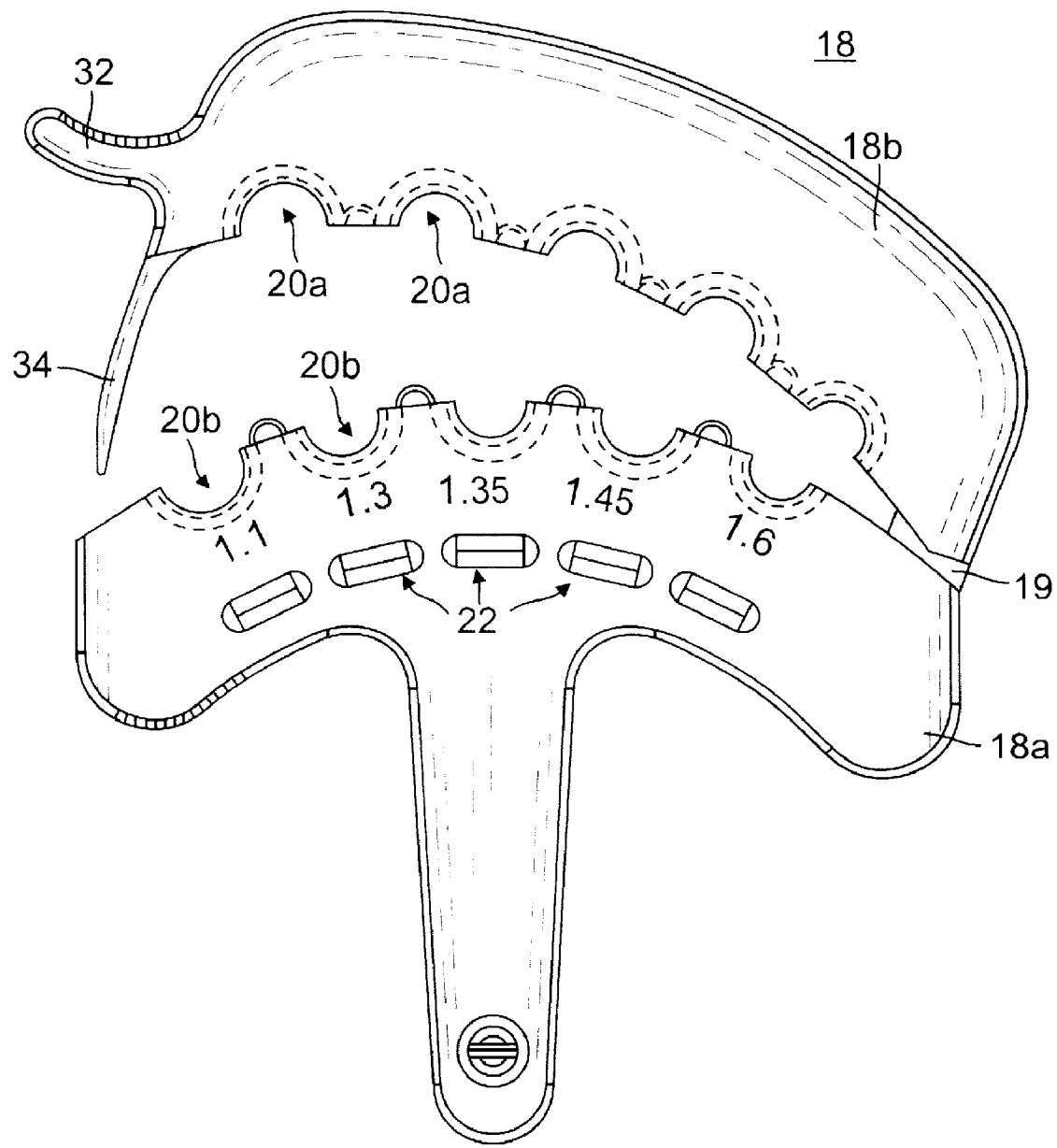
FIG. 4. Is a top plan view of the base 18 depicting the base halves 18a, 18b in an open configuration through the use of a hinge 19, which results in aperture halves 20a, 20b.
Figure 5:
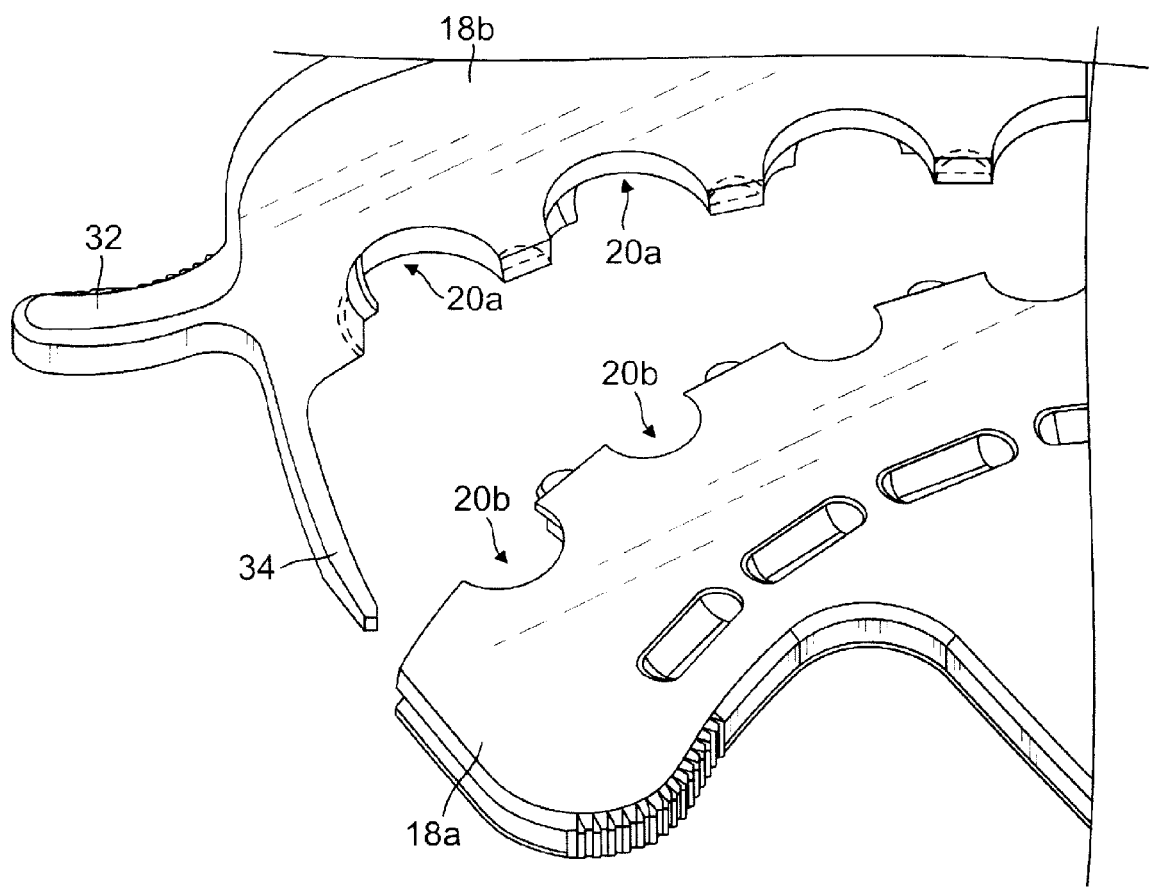
FIG. 5 depicts a partial perspective view of open base halves 18a, 18b aperture halves 20a, 20b, a preferred positioning of a handle 32, locking mechanism 34 and thumb grip 36 for ease of use.
Figure 6:
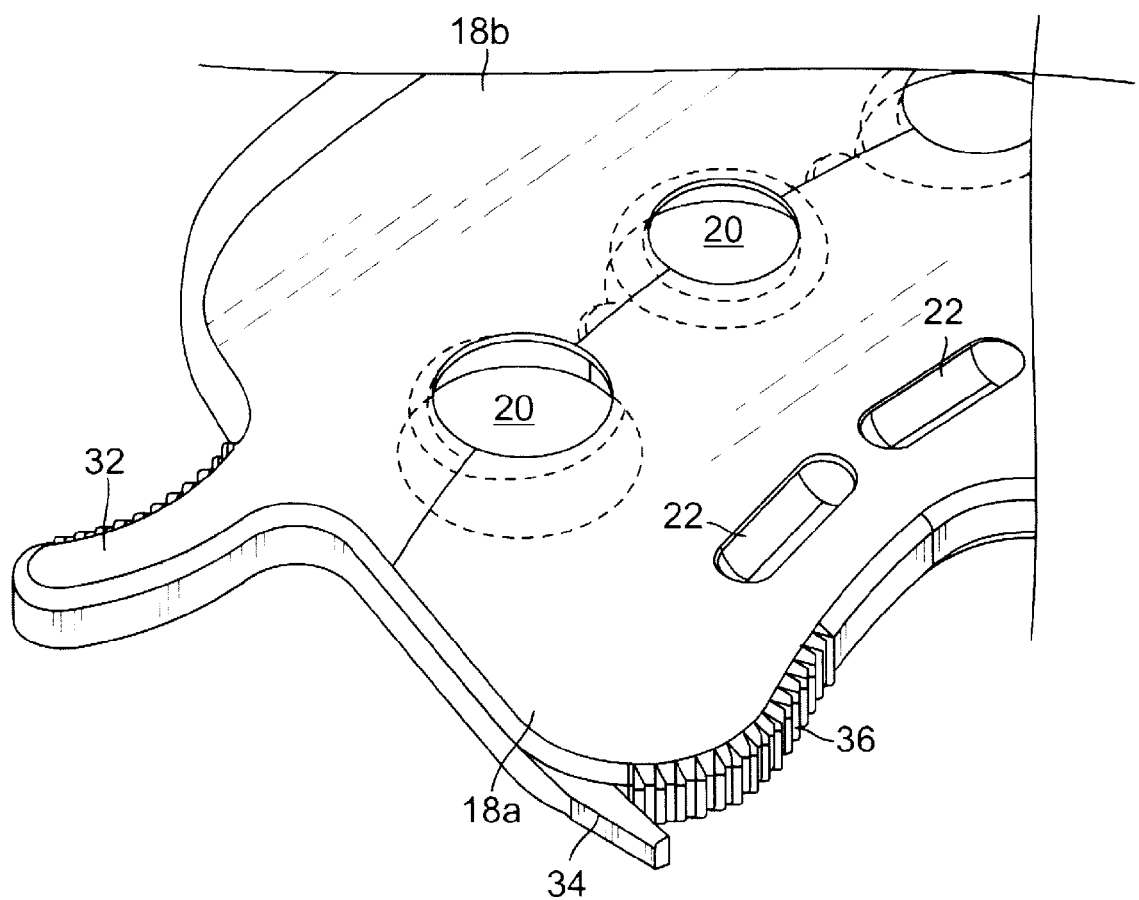
FIG. 6 depicts a partial perspective view of closed base halves 18a, 18b, handle 32 locking structure 34 and thumb grip 36.

FIGS. 4 and 5 depict the base halves 18a, 18b in an open configuration. The base halves 18a, 18b may be formed, such as by injection moulding then assembled or joined. The halves 18a, 18b are preferably joined at a hinge 19. Opening or closing the two base halves 18a, 18b may be further facilitated using a handle 32. As can be seen in comparison to the apertures 20 shown in FIGS. 1 and 2, in FIGS. 4 and 5 they are provided as aperture halves 20a, 20b. The opening of the base halves 18a, 18b permits the user to more easily insert a bell-shaped member 14 with surrounding prepuce into the region of the aperture halves 20a, 20b. Thus, using this configuration, the user can hold the prepuce over the bell-shaped member 14 and clamp the aperture halves 20a, 20b around the penis instead of threading the prepuce upward through an aperture as commonly performed in traditional circumcision devices. Closing the base halves 18a, 18b may be performed by pulling the handle 32 with a forefinger while positioning a thumb along a ridged grip 36 until a locking structure 34 locks the base 18 closed. The closed configuration is shown again in FIG. 6, which further demonstrates a preferred positioning of the handle 32 and rigged grip 36 which assists in closing and locking the halves 18a, 18b. The locking structure 34 may be any known in the art and may include complementary locking surfaces such as angled teeth and the like. The locking structure 34 reversibly locks the two base halves 18a, 18b and may be released by pressing the structure 34 away from the base half 18a.

Figure 10:
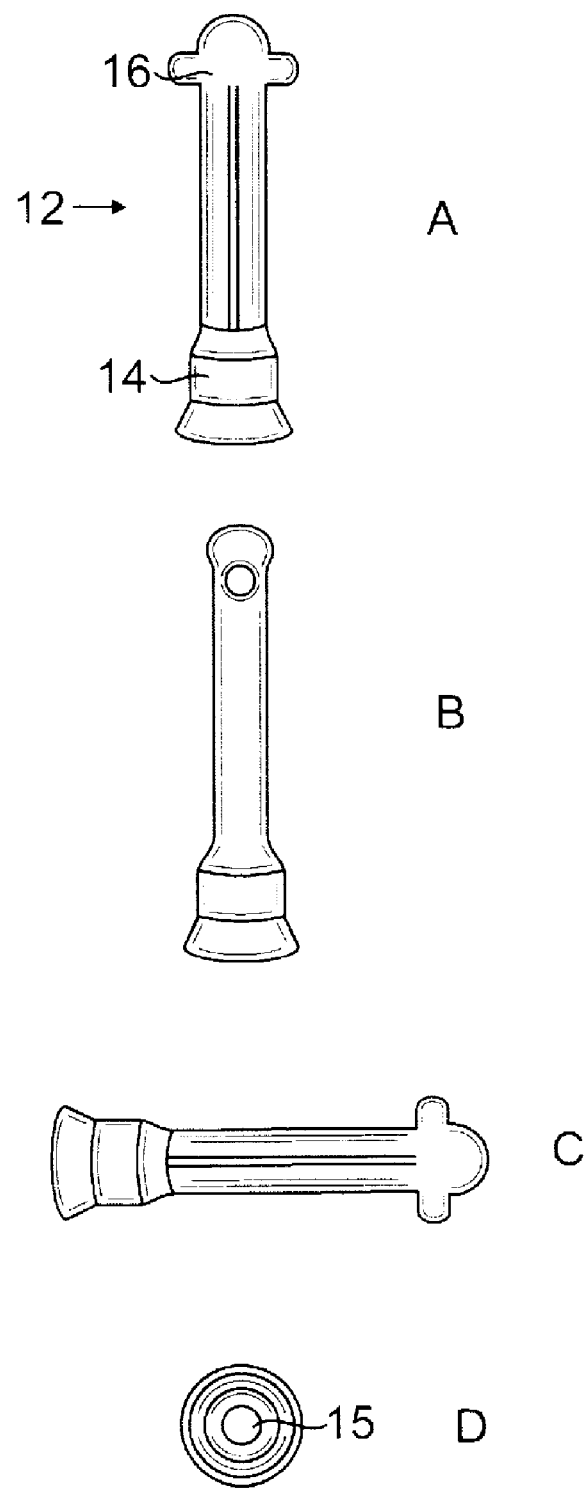
FIG. 10 depicts various views of the preferred rod 12 of the present invention.

A preferred rod 12 with bell-shaped member 14 and engagement structure 16 is depicted in FIG. 10. The bell-shaped member 14 is provided at the end opposite the engagement structure 16, also referred to as the lower end of the rod 12. The inner portion 15 of the bell-shaped member 14 accepts the tip of the penis, which allows the foreskin or prepuce to be drawn along the outer portion of the bell-shaped member 14. The bell-shaped member 14 can be fabricated then joined to the rod 12 or can be cast as a single piece using methods known to those skilled in the art to which the device 10 of the present invention belongs. Similarly, the engagement structure 16 may be any structure suitable for releasable engagement such as a cross-pin, spherical ball, polygon the like. The engagement structure 16 is preferably complementary to a grasping structure 28 on the distal portion 26a of the lever 24 or vice-versa.

Figure 7:
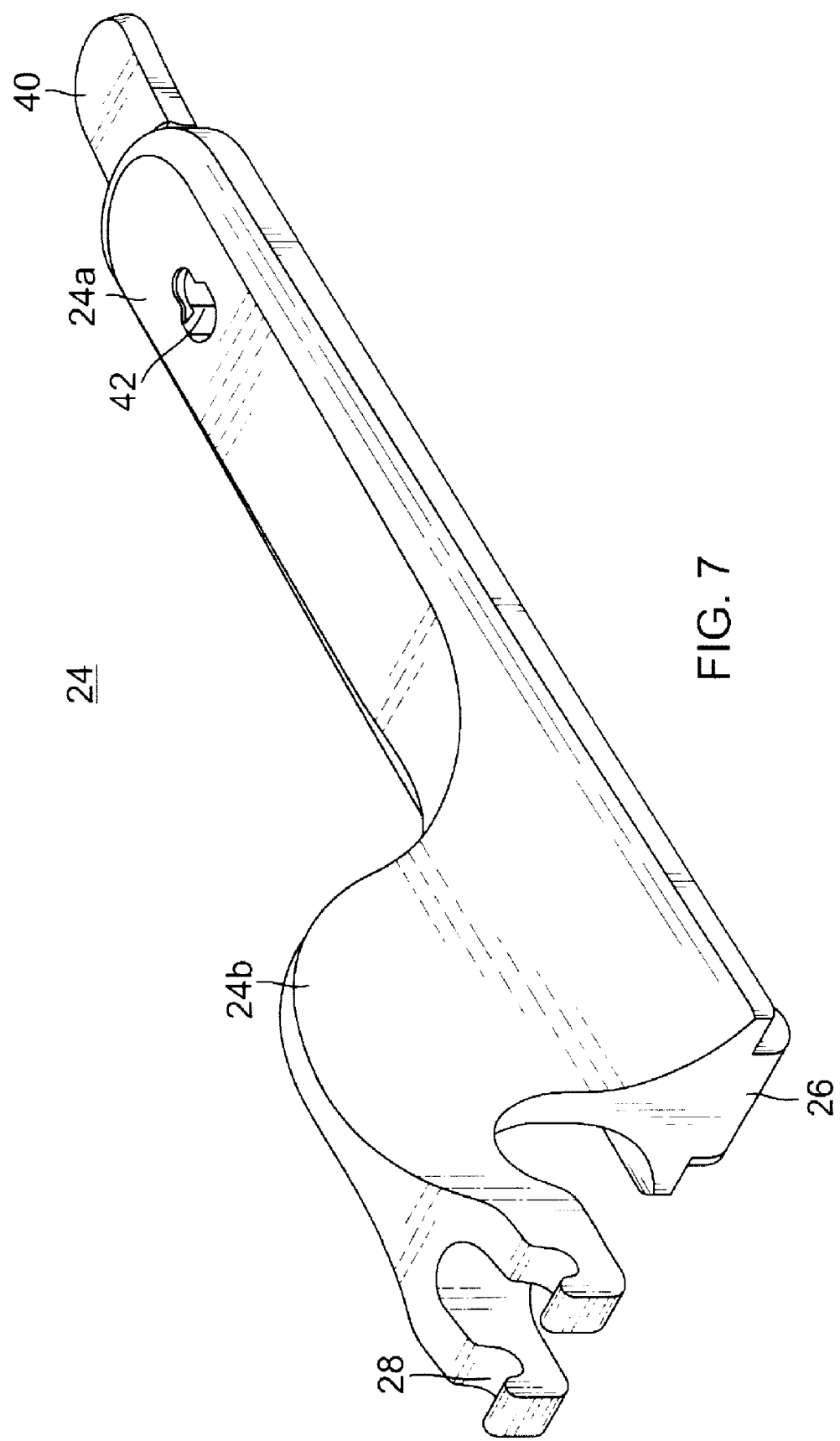
FIG. 7 depicts a perspective view of a lever 24 including a proximal end 24a, which includes a thumb handle 40 and adjusting aperture 42; and distal end 24b, which includes a fulcrum foot 26 and grasping structure 28.
Figure 8:
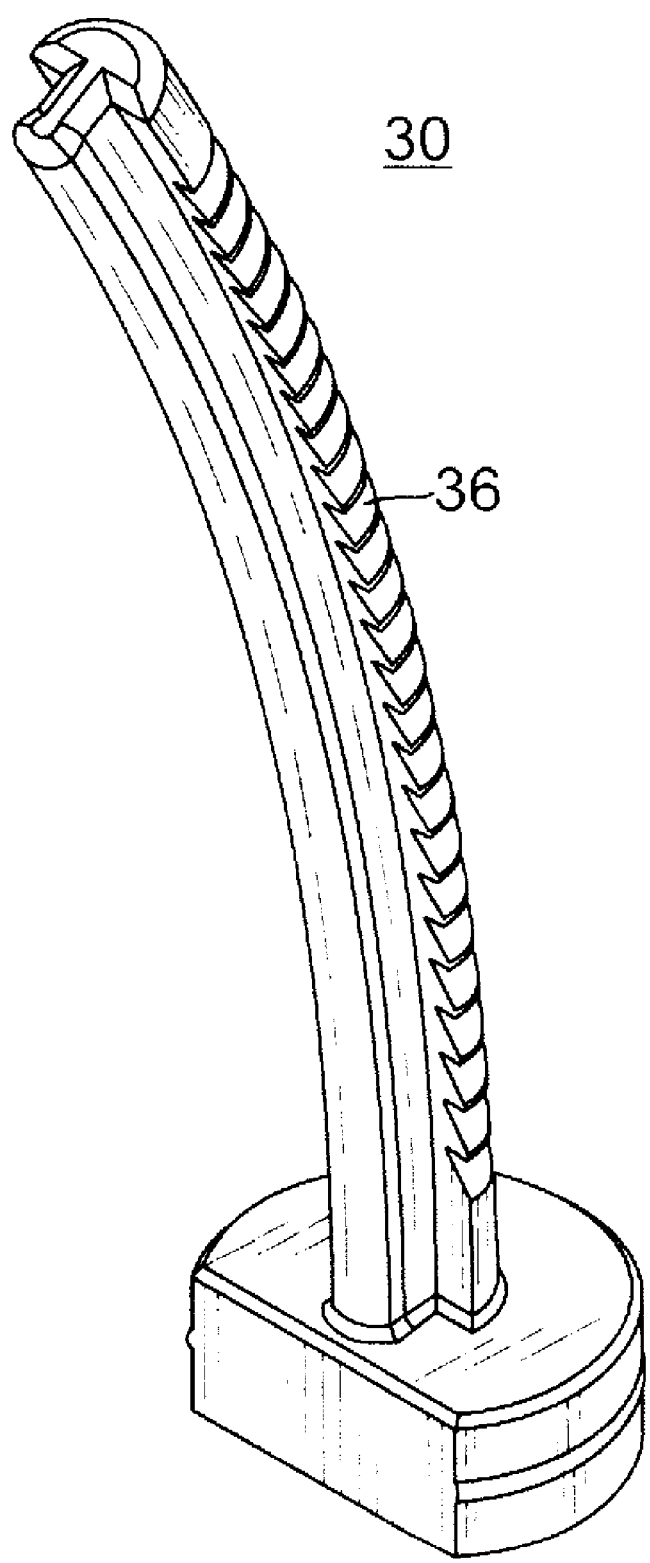
FIG. 8 depicts a perspective view of an adjusting structure 30 including angle teeth 26.

A preferred lever 24 is shown in FIG. 7, which includes a proximal end 24a and distal end 24b. The fulcrum foot 26 is shown at the distal end 24b which, referring back to FIGS. 1 and 2, may be inserted into any of the fulcrum recesses 22. The distal end 24b is also adapted for engagement with the rod 12 as shown in FIG. 1, such as by providing a grasping structure 28 which grasps the upper portion of the rod 12, such as at a cross pin, ball and the like referred to as an engagement structure 14. The proximal end 24a of the lever 24 may also include a thumb handle 40 to press downward, which facilitates pivoting of the lever 24 at the fulcrum foot 26. In preferred embodiments, the proximal end 24a is pressed or forced downward without substantial twisting or torsion. For instance a threaded bolt extending upward through the proximal end 24a of the lever 24 and corresponding tightening nut would result in torsional stress on the device 10, which would tend to twist the entire device 10 and thus cause patient discomfort. Since torsional stress may cause discomfort for the patient, a means that directly presses downward on the proximal end 24a of the lever 24 without rotation is preferred. An exemplary configuration includes an adjusting aperture 42 through which an adjusting structure 30, such as shown in FIG. 8, may be inserted. Referring to FIGS. 7 and 8, the adjusting structure 30 having angled teeth 36 may extend upward through the adjusting aperture 42 within the proximal end 24a. Thus, pressing downward on the proximal end 24a, such as at a thumb handle 40 would permit the mating of teeth 38 through the aperture 42. Releasing the teeth 38 may be performed by pulling or pushing the teeth 38 away from contact with the proximal end 24a. Alternative configurations for the adjusting structure 30 may include but are not limited to press-buttons complementary surfaces and the like.

In another aspect of the present invention a circumcision procedure is performed using the circumcision clamp 10. The head of the patient's penis is placed in the bell-shaped member 14 and the prepuce is pulled over the outer surface of the bell-shaped member 14. The base 18 is opened and the bell-shaped member 14 is placed into the aperture halves 20a, b. The base 18 is closed around the bell-shaped member 14 and prepuce. The fulcrum foot 26 of the lever 24 is placed in the recess 22 corresponding to the desired aperture 20. The rod 12 is engaged by the lever 24 and the proximal end 24a of the lever 24 is pressed downward thereby raising the distal end 24b and tightening the bell-shaped member 14 against the tapered aperture 20. The prepuce is surgically cut above the base 18. The proximal end 24a is release allowing the distal end 24b to lower and release the bell-shaped member 14 from the tapered aperture 20. The base 18 is opened and the rod 12 disengaged. The penis is removed from the bell-shaped member 14.

Circumcision Clamp with Actuating Structure Hinged at Midpoint

In a second aspect of the present invention a circumcision clamp is provided that includes an actuating structure hinged generally at its midpoint and remote from a base. Referring generally to FIGS. 9-12, the circumcision surgical clamp 100 includes a rod 12 having at one end an engagement structure 16 and at the opposing end a bell-shaped member 14, a base 120 including two arms 119a and 119b hinged 130 at one end and forming at least two apertures 126 when provided in a closed orientation, and an actuating structure 118 for raising the rod 12 such that the bell-shaped member 14 is raised towards the rim of the rimmed aperture 126.

Figure 9:
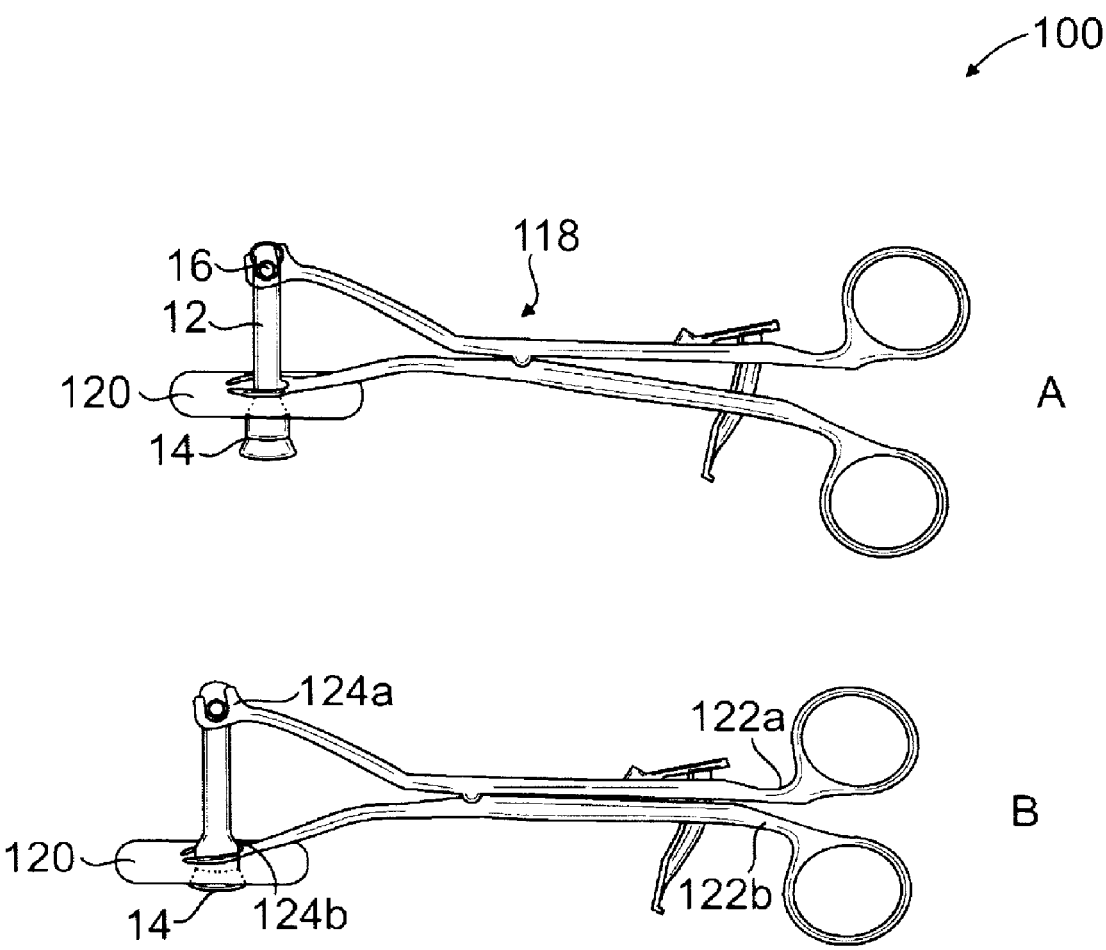
FIG. 9 is a side plan view of an alternative circumcision surgical clamp 100 of the present invention showing the ability of the rod 12 and more specifically the bell-shaped member 14 to be raised and lowered by raising and lowering the engagement structure 16 using the actuating structure 118.

Referring to FIGS. 9 and 10, at one end of the rod 12, also referred to as the upper end, exists an engagement structure 16. The engagement structure 16 allows the actuating structure 118 to engage the rod 12. The engagement structure 116 may be provided in any configuration that is able to engage an actuating structure 118 such that the actuating structure 118 may exert upward mechanical force upon the engagement structure 16 and thereby exert such upward force upon the rod 12, and thus raise the rod 12. Engagement typically involves the mating of two complementary surfaces such as tongue and groove, hook and loop, hook and cross pin, rod and aperture and the like. One skilled the art would be able to develop additional engagement structures 16 using the guidance provided herein, which are also encompassed by the present invention. In the preferred embodiment the engagement structure 16 is in the form of a cross pin. The engagement structure 16 may be fabricated then joined to the rod 12 using conventional casting and joining techniques such as welding, gluing and the like. The engagement structure 16 may also be joined to the rod 12 by non-permanent means. such as by insertion of a pin through a hole or aperture traversing the rod 12. Alternatively the engagement structure 16 may be cast as a single unit (e.g. injection moulded) in combination with the rod 12 using casting methods known to those skilled in the art to which the present invention belongs.

A bell-shaped member 14 is provided at the end opposite the engagement structure 16, also referred to as the lower end of the rod 12. The inner portion 15 of the bell-shaped member 14 accepts the tip of the penis, which allows the foreskin or prepuce to be drawn along the outer portion of the bell-shaped member 14. The bell-shaped member 14 may be fabricated then joined to the rod 12 or may be cast as a single piece using methods known to those skilled in the art to which the device 10 of the present invention belongs.

Figure 11:
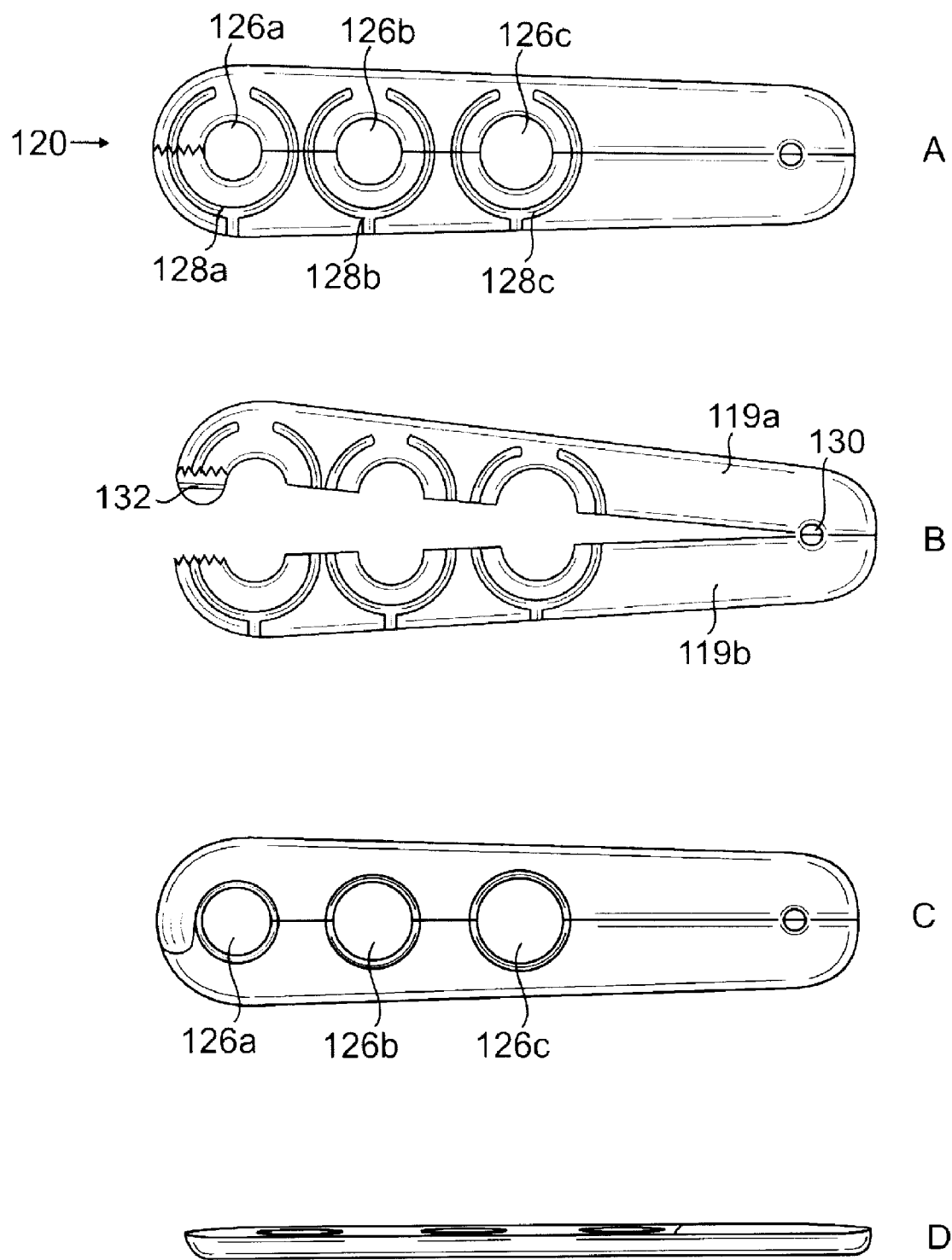
FIG. 11A is a top plan view of the base 120 shown in FIG. 9 in the closed position.
FIG. 11B is a top plan view of the base 120 in the open position.
FIG. 11C is a bottom plan view of the base 120 shown in FIG. 11A
FIG. 11D is an elevated side view of the base shown in FIG. 11A. Three rimmed apertures 126a, 126b and 126c are provided having different diameters from one another. The diameter of rimmed aperture 126a shown smaller than rimmed aperture 126b, which is shown smaller than rimmed aperture 126c. Equal sized recesses 128 a,b,c in an arced configuration are also depicted. The base 120 includes two arms 119a and 119b hinged 130 at one end and able to reversibly engage one another 132 at the opposing end. As can be viewed in FIG. 11C, the rimmed apertures 126 are tapered outward towards the bottom of the base 20.

Referring to FIG. 11, the base 120 includes two arms 119a and 119b joined at their distal ends by a hinge 130, which allows the base 120 to reversibly open and close. In some embodiments the base 120 is transparent allowing the practitioner to visually monitor the safety or comfort of the patient or the progress of the procedure. The base 120 provides the primary support for operation of the device 100 and should therefore be constructed from a rigid material. Preferably the base arms 119a, 119b are constructed from a metal alloy or injection moulded plastic.

The base arms 119 are hinged 130 at one end using conventional manufacturing techniques such that the base arms 119 are generally planar. The surface of the base 120 may be continuous or discontinuous and may include a variety of surface features such as recesses 128, throughbores, raised planes and the like. As used herein a hinge 130 also refers a pivot pin or a rotatable surface.

When in the closed position, the arms 119 form at least two rimmed apertures 126 having unequal diameters, though the diameters of the rimmed apertures 126 are in all cases greater than the diameter of the elongated portion of the rod 12, and smaller than the largest portion or outer lip of the bell-shaped member 14. Alternative embodiments utilize greater numbers of rimmed apertures 126 such as three, four or more, each having a different diameter, though the diameters of the rimmed apertures are in all cases greater than the diameter of the elongated portion of the rod 12, and smaller than the largest portion of the bell-shaped member 14 of the rod 12. The variation in size of rimmed apertures 126 allows the device to be used with a wide variety of penis sizes, as the variations in diameter size allows the operator to select the most appropriate aperture 126a, 126b or 126c through which to clamp the foreskin, and thus allow a single base 120 to accommodate a multitude of patients. The diameters of the apertures 126 may range from about ¼ inch or about ⅛ inch to about one, two or three inches, with diameters smaller and larger also being encompassed by the present invention. The diameters are preferably different sizes from one another. The rimmed apertures 126 are preferably upwardly tapered and thus tapered outwards towards the bottom of the base 120 to at least partially complement a portion of the bell-shaped member 14. Visual indicia 38 may indicate the size of the aperture 126.

The proximal ends of each of the two base members 119 reversibly engage 132 and may reversibly lock. The reversible engagement 132 or locking may be performed using complementary engaging surfaces or reversibly locking surfaces. As shown in FIG. 11, in one embodiment a locking means is provided having complementary locking angled teeth. In this embodiment the angled teeth allow the proximal ends to be joined by pushing one set of complementary angled teeth over the corresponding second. Release may occur by twisting or lifting one of the arms 119a or 119b generally upwards or downwards relative to the other in order to unlock the teeth, then pulling the proximal ends away from one another. The reversible engagement 132 or locking of the base members 119 ensures a stable surface upon which the bell-shaped member 14 of the rod 12 may exert force by pressing against the base 120 as the actuating structure 118 raises the rod 12 through the aperture 120.

Around or in the vicinity of the rimmed apertures 126 are recesses 128 or throughbores for insertion of the actuating structure 118 (e.g. the distal end 124b of the lower elongated member 134b). Recesses 128 are arranged in the vicinity of the rimmed apertures 126. The recesses 122 may be curved or arced, and may follow a portion of the perimeter of the rimmed aperture 126. In another alternative embodiment, the recesses 128 comprise a single, continuous groove surrounding the rimmed apertures 126. In another alternative embodiment, the recesses 128 are non-linear, such as circular or rectangular. The recesses 128 may be provided in any configuration that is able to receive an actuating structure 118 such that the actuating structure 118 may be securely positioned on the base 120 to raise the rod 12 through the aperture 126. Recesses 128 may be formed by drilling or milling into the base 120 to form a desired shape or depth, or alternatively the base 120 may be cast or injection-molded such that the recesses 128 are thereby created.

Figure 12:
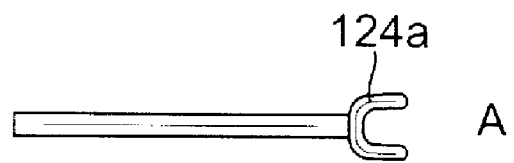
FIG. 12 depicts a configuration of the actuating structure 118 and parts thereof.
Figure 12:
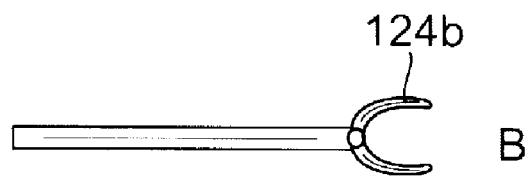
Figure 12:
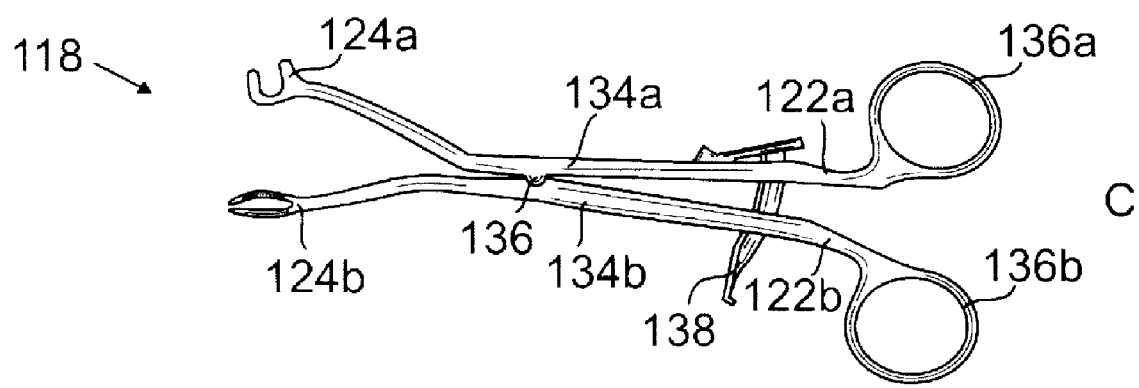
Figure 12:
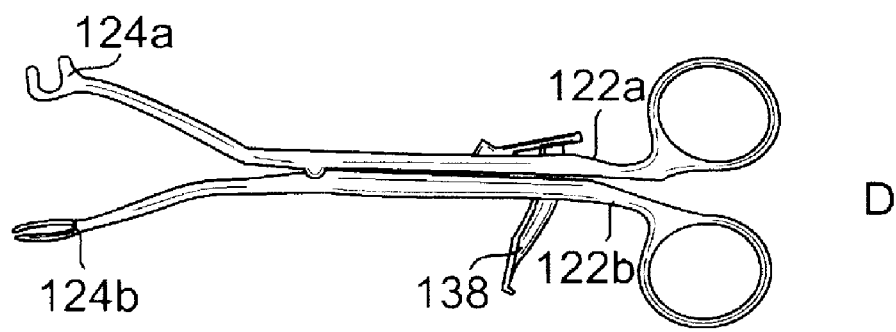

FIG. 12 depicts a preferred embodiment of the actuating structure 118 that is hinged at its midpoint. The actuating structure 118 includes two elongated members 134a and 134b hinged 136 near their midpoints or mid sections. The term "near their midpoints or mid sections" as used herein refers to the portion of the elongated members 134 that is between the distal end 124 and proximal end 122. The members 134 are arranged such that when the proximal ends 122 are maximally proximate and substantially parallel, the distal ends 124 are maximally opposed. The actuating structure 118 may be constructed using methods and materials known in the medical arts such as those used in the construction of hemostats and handheld retractors. As non-limiting examples, the actuating structure 118 may be constructed from metal, metal alloy such as stainless steel or aluminum, plastic and the like.

The proximal ends 122 form a handle 136 allowing the user to squeeze the proximal ends 122 together to raise the rod 12. Each proximal end 122 may be contoured for placement of a finger or thumb such as incorporating a finger loop. The proximal end 122 may further include a locking structure 138 allowing the actuating structure 118 to be locked in the closed or squeezed position such that the distal end 124a of the upper elongated member 134a raises the rod 12. Such locking structures 138 are known in the medical arts, for example those incorporated on hemostats, hand held retractors and the like, which are incorporated by reference and encompassed within the present invention.

One of the members (also referred to as the lower member) 134b is adapted at its distal end 124b for insertion into a recess 128 or throughbore in the base arm(s) 119. The distal end 124b of the lower member 134b stabilizes the actuating structure 118. The adaptation may be provided in a variety of configurations such as having a downward protrusion or a generally arced configuration as provided in FIG. 12 or any other configuration that ensures a secure engagement between the distal end 124b and the recesses 128. The configuration of the lower member's distal end 124b depends on the configuration of the corresponding recess 128 or throughbore. The configuration should be generally complementary. One skilled in the art to which the present invention belongs would recognize that the distal end 124b of the lower member 134b may include a single end for insertion into a single recess 128 or throughbore or a forked end having one or more forks for insertion into two or more recesses 128 or throughbores. The present invention includes a distal end 124b including one or more portions for insertion into one or more recesses 128 or throughbores for stabilization of the present invention. In the preferred embodiment the distal end 124b has an arc-like configuration that is complementary to a recess 128 having an arc-like configuration. In the preferred embodiment the actuating structure 118 is positioned approximately perpendicular to the base 120. Also preferred is a distal end 124b and complementary recess 128 that affect both arms 119 of the base 120 such that the distal end 124b applies force against each of the two arms 119.

The other member (also referred to as the upper member) 134a is adapted at its distal end 124a to engage the engagement structure 16 and thereby manipulate the rod 12 through one of the at least two rimmed apertures 126. The distal end 124a of the upper member 134a is provided in a configuration that is capable of the engagement with the engagement structure 16 such as having a complementary surface. In the preferred embodiments, the upper member 124a is adapted for placement under the engagement structure 16 such as a two pronged hook positionable under a cross pin or under a spherical engagement structure and the like. Therefore in the preferred embodiments the distal end 124a of the upper member 134a is actuated such that it lifts the rod 12 upwards however the present invention also includes embodiments where the upper member 134a is positioned above the rod 12 and pulls the rod 12 upwards. In further embodiments, the actuating structure 18 may include additional features such as an upward protrusion on the lower member to assist in pulling back the foreskin or prepuce for placement around the bell-shaped member.

In another aspect of the present invention a method of performing a circumcision is provided including providing the circumcision clamp 100 of the present invention, placing the head of a patient's penis in the bell-shaped member 14, pulling the foreskin over the outer portion of the bell-shaped member 14, closing the base 120 around the bell-shaped member 14 covered with the foreskin, inserting one of the distal ends 124b of the actuating structure 118 in the recess 128 of the base 120 and the engaging the rod's engagement structure 16 with the opposing distal end 24a, squeezing the handle of the actuating structure 118 to raise the bell-shaped member 14 against the rimmed aperture 126, and cutting the foreskin above the base 120.

Circumcision Surgical Kits

Embodiments of the invention are also directed to a kit for performing a circumcision procedure. The kit is an assemblage of materials or components. suitable for performing a method of an embodiment of the invention. Thus, in some embodiments the kit contains the circumcision clamp 10, 100 together with medical or surgical tools.

The exact nature of the components configured in the inventive kit depends on its intended purpose. For example, the kit can contain one or more surgical tools such as a scalpel, a hemostat, forceps, a dressing, disinfectant, and the like. The kit can be provided as a one time use kit or may be sterilized such as by autoclave one or more times for routine use.

Instructions for use may be included in the kit. "Instructions for use" typically include a tangible expression describing the technique to be employed in using the components of the kit to affect a desired outcome, such as performing a circumcision procedure. Optionally, the kit also contains other useful components, such as, for example, sterile gloves, sterile water, bandaging materials, or other useful paraphernalia as will be readily recognized by those of skill in the art.

The materials or components assembled in the kit can be provided to the practitioner stored in any convenient and suitable ways that preserve their operability and utility. For example the components can be provided at room temperature or lowered or raised temperatures. The components are typically contained in suitable packaging material(s). As employed herein, the phrase "packaging material" refers to one or more physical structures used to house the contents of the kit, such as inventive devices and the like. The packaging material is constructed by well known methods, preferably to provide a sterile, contaminant-free environment. The packaging materials employed in the kit are those customarily utilized in surgical procedure kits. As used herein, the term "package" refers to a suitable solid matrix or material such as glass, plastic, paper, foil, and the like, capable of holding the individual kit components. Thus, for example, a package can be a plastic container used to contain suitable quantities of an inventive device. The packaging material generally has an external label which indicates the contents and/or purpose of the kit and/or its components.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting example is provided to further illustrate the present invention. It should be appreciated by those of skill in the art that the technique disclosed in the example that follows represents an approach found to function well in the practice of the invention, and thus can be considered to constitute an example of a mode for its practice. However, those of skill in the art should, in light of the present disclosure, appreciate that many changes can be made in the specific embodiments that are disclosed and still obtain a like or similar result without departing from the spirit and scope of the invention.

Example 1

Circumcision with Clamp Including Rotational Selection of Aperture

The patient is assessed by the physician to determine the appropriate aperture for use based upon the size of the patient's penis. A local anesthetic is applied to the foreskin and penis, and the physician places the head of the patient's penis in the bell-shaped member. Then, the patient's foreskin is pulled over the outer portion of the bell-shaped member. With the base halves open the physician positions the bell-shaped member with foreskin within the chosen aperture halves. The base halves are clamped around the bell shaped member trapping a portion of the foreskin above the base. The lever is aligned towards the desired aperture and the fulcrum foot is positioned within the fulcrum recess. The distal portion of the lever engages the rod. The physician pushes down against the proximal end of the lever to raise the distal end and thus rod, which tightens the bell-shaped member against the tapered aperture. As the proximal end lowers the teeth of the adjusting structure feed against and thus attach to the proximal end. Using a scalpel, the foreskin is cut and removed above the base. The proximal end is released by disengaging the teeth of the adjusting structure. The base halves are opened and the bell-shaped member removed from the patient. A dressing is applied to the patient as desired.

Example 2

Circumcision with Clamp Including Actuating Structure Hinged at Midpoint

The patient is assessed by the physician to determine the appropriate aperture to use, based upon the size of the patient's penis. A local anesthetic is applied to the foreskin and penis, and the physician places the head of the patient's penis in the bell-shaped member. Then, the patient's foreskin is pulled over the outer portion of the bell-shaped member. Next, the physician closes the base around the bell-shaped member covered with the foreskin and inserts the distal end of the lower member forming actuating structure in the recess of the base. The handle is squeezed to raise the bell-shaped member against the rimmed aperture, thus securing the foreskin in place. The operator then cuts the foreskin above the base and applies a disinfectant to the wound site. The operator then releases the actuating structure, engaged base arms and applies a dressing to the wound.

What is claimed is:

1. A circumcision device comprising:
 a) a rod comprising a bell-shaped member at a first end for receiving the head of a penis and an engagement structure at an opposing end;
 b) a base comprising at least three selecting positions aligned along an arc, wherein each selecting position comprises:
  i) an upwardly tapered aperture of unique diameter, wherein each upward taper is complementary to said bell-shaped member, and
  ii) a fulcrum recess in radial alignment with said aperture;
 c) a lever comprising:
  i) a proximal end that radially selects between each of said at least three selecting positions and that remains in radial alignment with each aperture at any selecting position,
  ii) a distal end comprising a fulcrum foot complementary to each fulcrum recess and adapted for engagement with said rod; and
 d) an adjustment structure for raising and lowering an engaged rod by pivoting said lever at a selected fulcrum recess.

2. The circumcision device according to claim 1, wherein said at least three selecting positions comprise at least five selecting positions.

3. The circumcision device according to claim 2, wherein each of said at least five selecting positions further comprise indicia in radial alignment with each aperture.

4. The circumcision device according to claim 1, wherein said base comprises two hinged arms and a locking structure that reversibly locks said two hinged arms in a closed configuration.

5. The circumcision device according to claim 4, further comprising a handle positioned on at least one of said two arms and opposite the hinge for opening and closing the hinge.

6. The circumcision device according to claim 1, wherein said adjustment structure extends upward from said base and comprises a plurality of angled teeth, further wherein said proximal end of said lever comprises an adjustment aperture through which said adjustment structure extends.

7. The circumcision device according to claim 6, wherein said adjustment aperture comprises a smaller portion for locking said adjustment structure and a larger portion for releasing said adjustment structure.

8. The circumcision device according to claim 1, wherein said fulcrum recess is a shared recess between each of said at least three selecting positions.

9. A circumcision kit, comprising:
 a) a circumcision device comprising:
  i) a rod comprising a bell-shaped member at a first end for receiving the head of a penis and an engagement structure at an opposing end;
  ii) a base comprising at least three selecting positions aligned along an arc, wherein each selecting position comprises:
   (1) an upwardly tapered aperture of unique diameter, wherein each upward taper is complementary to said bell-shaped member, and
   (2) a fulcrum recess in radial alignment with said aperture;
  iii) a lever comprising:
   (1) a proximal end that radially selects between each of said at least three selecting positions and that remains in radial alignment with each aperture at any selecting position,
   (2) a distal end comprising a fulcrum foot complementary to each fulcrum recess and adapted for engagement with said rod;
  iv) an adjustment structure for raising and lowering an engaged rod by pivoting said lever at a selected fulcrum recess; and
 b) a scalpel.

* * * * *